US00PP19288P2

(12) United States Plant Patent
Verwer

(10) Patent No.: US PP19,288 P2
(45) Date of Patent: Oct. 7, 2008

(54) ***DAHLIA* PLANT NAMED 'GALLERY LA TOUR'**

(50) Latin Name: *Dahlia hybrida*
Varietal Denomination: Gallery La Tour

(75) Inventor: Aad W. M. Verwer, DL Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/890,466

(22) Filed: Aug. 6, 2007

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent L Bell
(74) *Attorney, Agent, or Firm*—C. A. Whealy

(57) ABSTRACT

A new and distinct cultivar of *Dahlia* plant named 'Gallery La Tour', characterized by its compact, upright, somewhat outwardly spreading and mounded plant habit; freely branching growth habit; dark-colored foliage; freely flowering habit; decorative-type inflorescence form; inflorescences with light purple-colored ray florets; and good postproduction longevity and garden performance.

2 Drawing Sheets

Botanical designation: *Dahlia hybrida.*
Cultivar denomination: 'Gallery La Tour'.

BACKGROUND OF THE INVENTION

The present invention relates to a new and distinct cultivar of *Dahlia* plant, botanically known as *Dahlia hybrida,* and hereinafter referred to by the name 'Gallery La Tour'.

The new *Dahlia* is a product of a planned breeding program conducted by the Inventor in Lisse, The Netherlands. The objective of the breeding program is to create new compact container-type *Dahlia* cultivars that have a freely branching growth habit, early and freely flowering habit, decorative inflorescence form, attractive ray floret coloration, and good postproduction longevity and garden performance.

The new *Dahlia* originated from a cross-pollination in Lisse, The Netherlands during the summer of 2002 of the *Dahlia hybrida* cultivar Melody Harmony, disclosed in U.S. Plant Pat. No. 18,423, as the female, or seed, parent with the *Dahlia hybrida* cultivar Gallery Salvador, disclosed in U.S. Plant Pat. No. 10,501, as the male, or pollen, parent. The new *Dahlia* was discovered and selected by the Inventor as a single flowering plant within the progeny of the stated cross-pollination in a controlled environment in Lisse, The Netherlands during the summer of 2003.

Asexual reproduction of the new *Dahlia* by cuttings since the spring of 2004 in a controlled environment in Lisse, The Netherlands, has shown that the unique features of this new *Dahlia* are stable and reproduced true to type in successive generations.

SUMMARY OF THE INVENTION

The cultivar Gallery La Tour has not been observed under all possible environmental conditions. The phenotype may vary somewhat with variations in environment such as temperature and light intensity, without, however, any variance in genotype.

The following traits have been repeatedly observed and are determined to be the unique characteristics of 'Galley La Tour'. These characteristics in combination distinguish 'Gallery La Tour' as a new and distinct cultivar of *Dahlia:*

1. Compact, upright, somewhat outwardly spreading and mounded plant habit.
2. Freely branching growth habit.
3. Dark-colored foliage.
4. Freely flowering habit.
5. Decorative-type inflorescence form.
6. Inflorescences with light purple-colored ray florets.
7. Good postproduction longevity and garden performance.

Plants of the new *Dahlia* differ from plants of the female parent, the cultivar Melody Harmony, in the following characteristics:

1. Plants of the new *Dahlia* are more compact than plants of the cultivar Melody Harmony.
2. Plants of the new *Dahlia* are more freely branching than plants of the cultivar Melody Harmony.
3. Plants of the new *Dahlia* and the cultivar Melody Harmony differ in leaf and ray floret coloration.
4. Plants of the new *Dahlia* have smaller inflorescences than plants of the cultivar Melody Harmony.

Plants of the new *Dahlia* differ from plants of the male parent, the cultivar Gallery Salvador, in the following characteristics:

1. Plants of the new *Dahlia* are stronger than plants of the cultivar Gallery Salvador.
2. Plants of the new *Dahlia* and the cultivar Gallery Salvador differ in leaf coloration.

Plants of the new *Dahlia* can be compared to plants of the *Dahlia* cultivar Melody Dixie, disclosed in U.S. Plant Pat. No. 12,911. In side-by-side comparisons conducted in Lisse, The Netherlands, plants of the new *Dahlia* differed from plants of the cultivar Melody Dixie in the following characteristics:

1. Plants of the new *Dahlia* were more compact than plants of the cultivar Melody Dixie.

2. Plants of the new *Dahlia* were more freely branching than plants of the cultivar Melody Dixie.
3. Plants of the new *Dahlia* and the cultivar Melody Dixie differed in leaf and ray floret coloration.

BRIEF DESCRIPTION OF THE PHOTOGRAPHS

The accompanying photographs illustrate the overall appearance of the new *Dahlia*. The photographs show the colors as true as it is reasonably possible to obtain in colored reproductions of this type. Colors in the photographs may differ slightly from the color values cited in the detailed botanical description which accurately describe the colors of the new Dahlia.

The photograph on the first sheet comprises a side perspective view of a typical flowering plant of 'Gallery La Tour' grown in a container.

The photograph on the second sheet is a close-up view of typical inflorescences of 'Gallery La Tour'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer and autumn in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about three to four months old when the photographs and description were taken.

Botanical classification: *Dahlia hybrida* cultivar Gallery La Tour.

Parentage:

*Female, or seed, parent.*—*Dahlia hybrida* cultivar Melody Harmony, disclosed in U.S. Plant Pat. No. 18,423.

*Male, or pollen, parent.*—*Dahlia hybrida* cultivar Gallery Salvador, disclosed in U.S. Plant Pat. No. 10,501.

Propagation:

*Type.*—By cuttings.

*Time to initiate roots, summer.*—About ten days at temperatures of about 20° C. to 22° C.

*Time to initiate roots, winter.*—About twelve days at temperatures of about 20° C. to 22° C.

*Time to produce a rooted young plant, summer.*—About 20 days at temperatures of about 20° C. to 22° C.

*Time to produce a rooted young plant, winter.*—About 24 days at temperatures of about 20° C. to 22° C.

*Root description.*—Medium in thickness, fleshy; 157C in color. If tubers develop, they are corky in texture and 199B in color.

*Rooting habit.*—Moderate branching; moderately dense.

Plant description:

*Plant form/growth habit.*—Compact, upright to somewhat outwardly spreading; mounded plant form. Freely basal branching with about six primary lateral branches; dense and bushy plant habit. Inflorescences held above the foliage on strong peduncles. Vigorous growth habit.

*Plant height.*—About 30 cm.

*Plant diameter or spread.*—About 30 cm.

*Lateral branches.*—Length: About 25 cm. Diameter: About 1.8 cm. Internode length: About 2 cm to 7 cm. Aspect: Erect to about 20° from vertical. Strength: Strong. Texture; Smooth, glabrous. Color: 187A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Serrate and divided; sinuses divergent.

*Length.*—Single leaves: About 11 cm. Compound leaves with three leaflets; About 15 cm. Compound leaves with five leaflets: About 22 cm.

*Width.*—Single leaves: About 4.6 cm. Compound leaves with three leaflets: About 9 cm. Compound leaves with five leaflets: About 16 cm.

*Venation pattern.*—Pinnate.

*Texture, upper and lower surfaces.*—Smooth, glabrous.

*Color.*—Developing foliage, upper surface: 139A. Developing foliage, lower surface: 191A. Fully expanded foliage, upper surface: 147A overlain with 187C; venation, 187B. Fully expanded foliage, lower surface: Close to 191A; venation, 187C.

*Petiole length.*—Single leaves: About 1 cm. Compound leaves with three leaflets: About 5 cm. Compound leaves with five leaflets: About 7 cm.

*Petiole diameter.*—Single leaves: About 2 mm. Compound leaves with three leaflets: About 2 mm. Compound leaves with five leaflets: About 3 mm.

*Petiole texture, upper and lower surfaces.*—Smooth, glabrous.

*Petiole color, upper surface.*—183A.

*Petiole color, lower surface.*—166A.

Inflorescence description:

*Appearance.*—Rotate double inflorescence form with ray and disc florets. Inflorescences positioned above the foliage on strong peduncles. Inflorescences face upright to slightly outwardly. Freely flowering habit; about 30 inflorescences develop per plant. Inflorescences persistent. Inflorescences not fragrant.

*Time to flower.*—Plants flower continuously during the summer and autumn in The Netherlands.

*Post-production longevity.*—Inflorescences maintain good substance for about 22 days on the plant and for about six days as a cut flower.

*Inflorescence bud.*—Height: About 1.3 cm. Diameter: About 1.8 cm. Shape: Oblate. Color: Towards the base, 146B; towards the apex, 178B.

*Inflroescence size.*—Diameter: About 9.5 cm. Depth (height): About 4.4 cm. Disc diameter: About 1.1 cm. Receptacle height: About 1.4 cm. Receptacle diameter: About 1.8 cm.

*Ray florets.*—Length: About 4 cm. Width: About 1.8 cm. Shape: Ovate. Apex: Mucronate. Base: Attenuate. Aspect: Initially upright to roughly perpendicular to the peduncle to reflexed. Texture, upper and lower surfaces: Smooth, glabrous; satiny to velvety. Number of ray florets per inflorescence: About 120 arranged in about twelve whorls. Color: When opening, upper surface: Towards the base, 3C; midsection, 2D; towards the apex, 78A. When opening, lower surface: 2D; towards the apex, 78B. Fully opened, upper surface: Towards the base, 21B, mid-section, 75C; towards the apex, 78B. Color becoming closer to 75B with development. Fully opened, lower surface: 75B; towards the apex, 78B to 78C.

*Disc florets.*—Shape: Tubular; apex dentate. Length: About 1.4 cm. Diameter: About 1 mm. Number of disc florets per inflorescence: About seven to ten. Color: Immature: Towards the apex, 23A; mid-section, 2B; towards the base, 1C. Mature: Towards the apex, 22A; mid-section, 2B; towards the base, 1C.

*Phyllaries.*—Quantity per inflroescence: About nine arranged in a single whorl. Length: About 1.6 cm. Width: About 5 mm. Shape: Oblanceolate. Apex: Acuminate. Base: Attenuate. Margin: Entire. Texture, upper and lower surfaces: Smooth, glabrous; satiny. Color, upper and lower surfaces: Towards the apex, 200A; towards the base, 187C.

*Peduncles.*—Length: Terminal peduncle: About 9 cm. Fourth peduncle: About 11 cm. Seventh peduncle: About 13 cm. Diameter: About 3 mm. Strength: Strong. Aspect: Erect to about 20° from vertical. Texture: Smooth, glabrous. Color: 187A.

*Reproductive organs.*—Androecium: Quantity per disc floret: Five. Filament length: About 7 mm. Filament color: 2D. Anther shape: Lanceolate. Anther length: About 5 mm. Anther color: 17C. Pollen amount: Scarce. Pollen color: 21B. Gynoecium: Quantity per ray or disc floret: One. Pistil length: About 2.6 mm. Stigma shape: Lanceolate. Stigma color: 12A. Style length: About 3 mm. Style color: 150B. Ovary color: 9B.

*Seeds.*—Seed development has not been observed.

Disease/pest resistance: Plants of the new *Dahlia* have not been shown to be resistant to pathogens and pests common to *Dahlia.*

Garden performance: Plants of the new *Dahlia* have exhibited good tolerance to rain and wind and have been observed to tolerate temperatures from about 0° C. to about 45° C.

It is claimed:

1. A new and distinct *Dahlia* plant named 'Gallery La Tour' as illustrated and described.

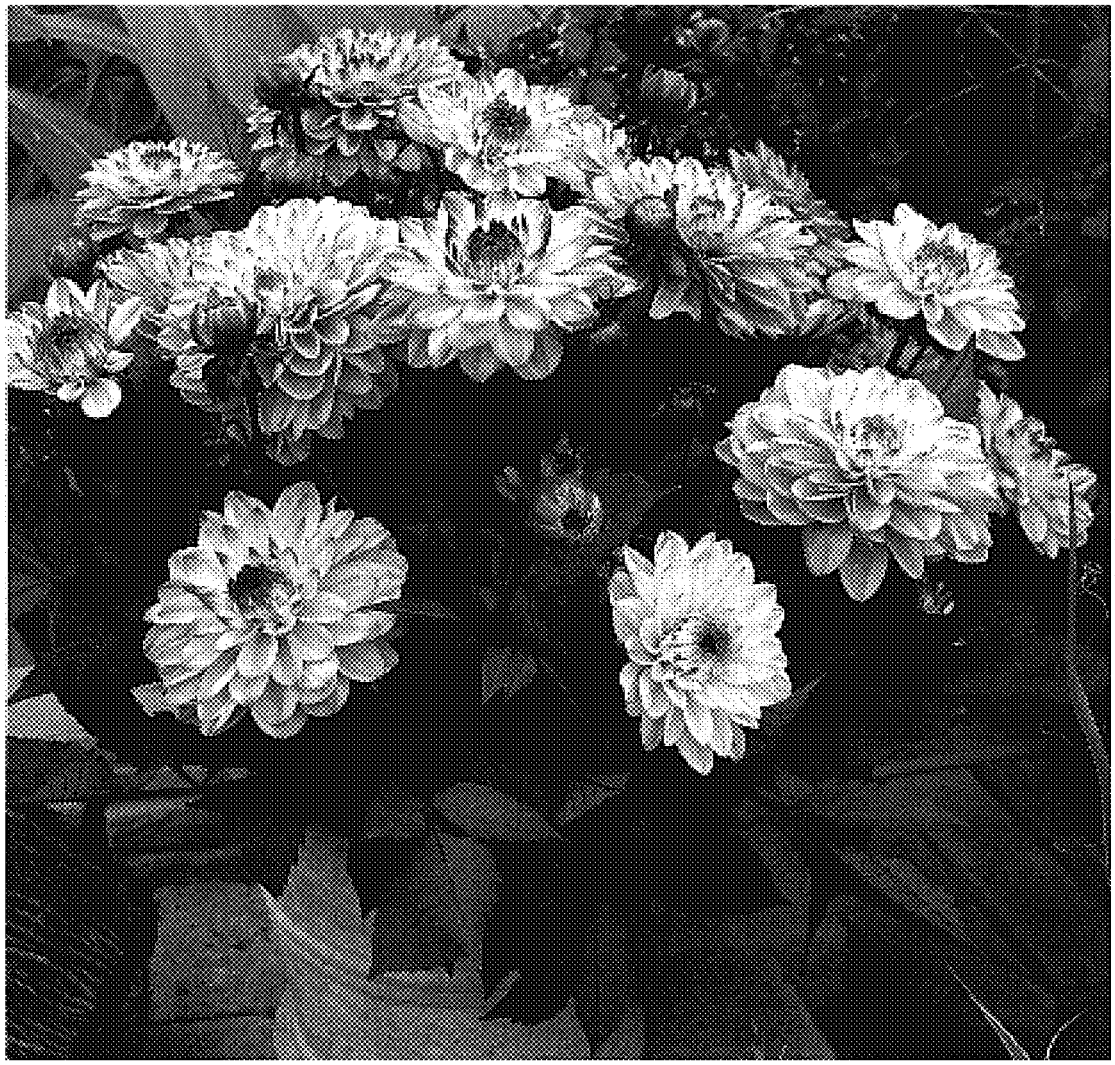

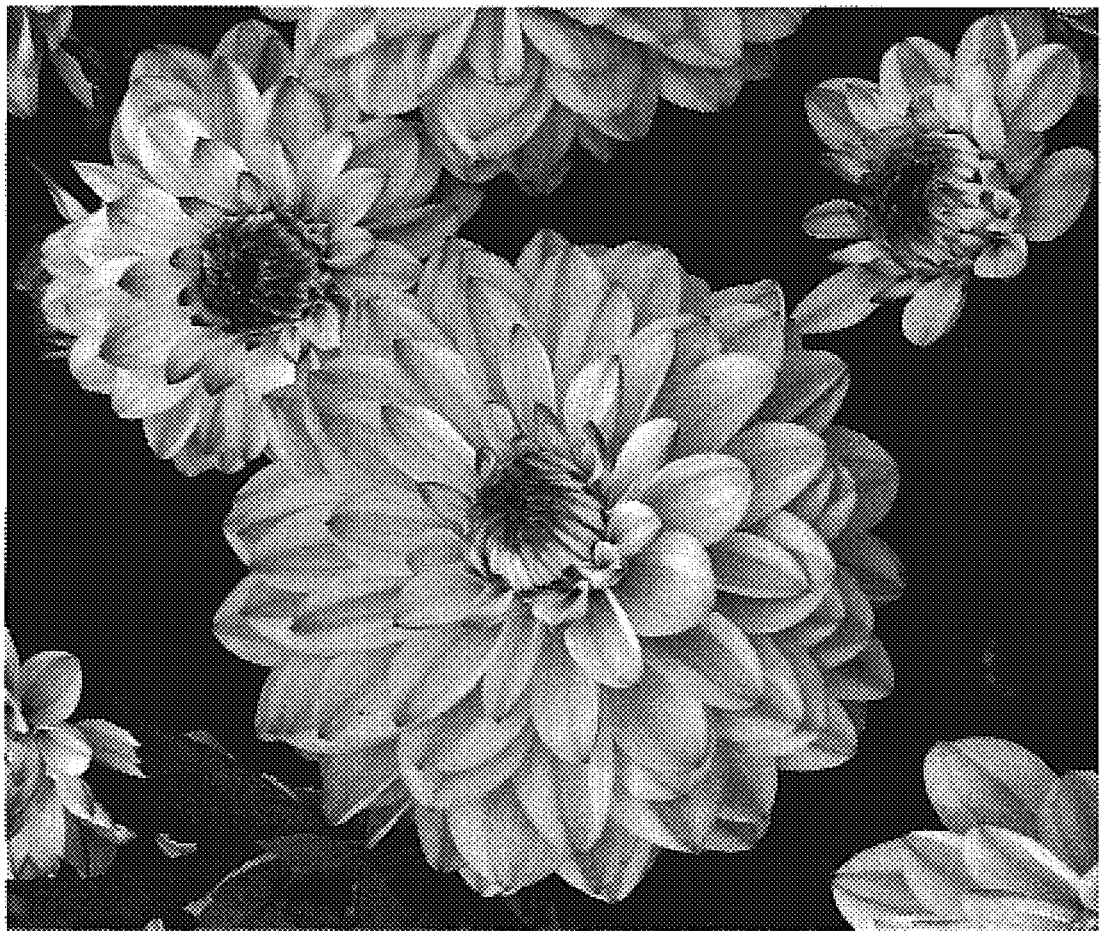

* * * * *